US010398359B2

(12) United States Patent
Dumanyan et al.

(10) Patent No.: US 10,398,359 B2
(45) Date of Patent: Sep. 3, 2019

(54) MOVEMENT ANALYSIS SYSTEM, WEARABLE MOVEMENT TRACKING SENSORS, AND ASSOCIATED METHODS

(71) Applicant: BioMetrix LLC, Durham, NC (US)

(72) Inventors: Ivonna Dumanyan, Vineland, NJ (US); Gabrielle Levac, Mount Airy, NC (US)

( * ) Notice: Subject to any disclaimer, the term of this patent is extended or adjusted under 35 U.S.C. 154(b) by 401 days.

(21) Appl. No.: 15/209,288

(22) Filed: Jul. 13, 2016

(65) Prior Publication Data

US 2017/0014049 A1 Jan. 19, 2017

Related U.S. Application Data

(60) Provisional application No. 62/191,866, filed on Jul. 13, 2015.

(51) Int. Cl.

*A61B 5/00* (2006.01)
*A61B 5/11* (2006.01)

(52) U.S. Cl.

CPC ............. *A61B 5/112* (2013.01); *A61B 5/1114* (2013.01); *A61B 5/486* (2013.01); *A61B 5/684* (2013.01); *A61B 5/6833* (2013.01); *A61B 5/7203* (2013.01); *A61B 5/7242* (2013.01); *A61B 5/746* (2013.01); *A61B 2560/0209* (2013.01); *A61B 2562/0219* (2013.01); *A61B 2562/164* (2013.01); *A61B 2562/166* (2013.01)

(58) Field of Classification Search

CPC ......... A61B 5/11; A61B 5/112; A61B 5/1123; A61B 24/0003; A61B 5/6833; A61B 5/684; A61B 5/1114; A61B 5/7203; A61B 5/7242; A61B 5/746; A61B 2560/0209; A61B 2562/164; A61B 2562/166; A61B 2562/0219

See application file for complete search history.

(56) References Cited

U.S. PATENT DOCUMENTS

| | | | | |
|---|---|---|---|---|
| 6,571,193 | B1 * | 5/2003 | Unuma | A43B 3/0005 340/853.2 |
| 8,165,844 | B2 | 4/2012 | Luinge et al. | |
| 8,229,226 | B2 | 7/2012 | Chuang et al. | |
| 8,510,584 | B1 | 8/2013 | Wright | |
| 8,766,977 | B2 * | 7/2014 | Kim | G06T 7/20 345/420 |
| 8,818,753 | B2 * | 8/2014 | Yuen | H04W 4/023 702/160 |

(Continued)

FOREIGN PATENT DOCUMENTS

WO WO-2009061283 A2 5/2009

*Primary Examiner* — Max F Hindenburg

(74) *Attorney, Agent, or Firm* — Alston & Bird LLP

(57) ABSTRACT

A binodal wireless sensor provides biomechanics feedback focused on movement tracking for the purpose of facilitating enhanced user training and recovery decisions. The sensing device and methods of use differs distinctly from current devices by utilizing a plurality of inertial sensors within a single, non-rigid unit to, among other things, identify a segment's position in space, identify internal movement and stability such as torsion, bending, shear movement, etc. in the segment, and/or between two segments. The unit includes data storage, wireless transmission, rechargeable battery, local processing and data collection sensors. The unit relays data to an intelligent device that provides feedback to the user.

11 Claims, 10 Drawing Sheets

(56) References Cited

U.S. PATENT DOCUMENTS

| | | | | |
|---|---|---|---|---|
| 8,892,401 | B2 * | 11/2014 | Yuen | G01C 22/006 702/179 |
| 9,302,170 | B2 * | 4/2016 | Balakrishnan | A61B 5/7246 |
| 9,681,827 | B2 * | 6/2017 | Huang | A61B 5/0022 |
| 10,016,165 | B2 * | 7/2018 | Hagiwara | A61B 5/6898 |
| 10,126,427 | B2 * | 11/2018 | Pekonen | G01C 22/006 |
| 2008/0146968 | A1 | 6/2008 | Hanawaka et al. | |
| 2009/0171180 | A1 | 7/2009 | Pering et al. | |
| 2009/0204031 | A1 | 8/2009 | McNames et al. | |
| 2009/0278791 | A1 | 11/2009 | Slycke et al. | |
| 2014/0228664 | A1 | 8/2014 | Alcazar | |

* cited by examiner

Sensor Frame

Coordinate frame relative to sensor device

User performs Calibration Protocol

1. Move hips back
Isolate movement in frontal plane

2. Stand in anatomically neutral position

Body Frame in relation to User's Body Segments

Transform Sensor Coordinate Frame relative to calibrated alignment of user's body segments Torsion within a segment Point 1 at position a
Point 2 at position b Point 1 is stationary at position a
Point 2 moves a quantifiable amount to position c Each sensor may be configured independently from the other sensors to optimize performance at the placement.

1. 100hz, 8G
2. 50hz, 2G
3. 50hz, 4G

Sensors may independently change settings based on user action to optimize performance.

1. PREPARING TO THROW 2. THROWING 3. STANDING

D1: 100hz, 16G
D2: 100hz, 4G
D3: 50hz, 4G

D1: 450hz, 100G
D2: 150hz, 8G
D3: 50hz, 4G

D1: 100hz, 8G
D2: 50hz, 2G
D3: 50hz, 4G

MOVEMENT ANALYSIS SYSTEM, WEARABLE MOVEMENT TRACKING SENSORS, AND ASSOCIATED METHODS

FIELD OF INVENTION

Embodiments relate to a movement analysis system which measures and analyzes key metrics using wearable movement tracking sensors.

BACKGROUND

To increase the accuracy of a gait analysis, technology must become increasingly sensitive to detect and accurately represent the appropriate biomechanics. Moreover, gait analysis technologies must remain easy and convenient to use in everyday activities. Current state of the art biomechanics analysis and motion capture technologies utilize a plurality of cameras and/or rigid units containing one inertial sensor deployed in a network to capture the position of a body segment in three-dimensional space. There exists several drawbacks to these historical techniques of conducting gait analyses.

For instance, motion capture systems tend to require controlled environments that can be both costly and limiting. Because the motion systems often utilize a plurality of cameras that cannot be moved as they are calibrated based on location, users may not be able to measure their biomechanics in their regular environments. Therefore, athletes may not be able to measure their biomechanics during training and patients in recovery likely would not be able to monitor their movement in their own home without significant cost.

Similarly, systems that utilize a single inertial sensor are limited in the information that can be provided and in the accuracy of that information. Placement of sensors generally can prove an arduous task. Misalignment during placement may be common to those not skilled in the art and will likely alter the results of the analysis. Rigid sensor bodies may not move in motion with the body and therefore may impede the ability to accurately measure various movements. Large and bulky designs may add to inaccuracies by increasing the noise and creating a level of intrusiveness that makes it difficult to perform regular functions. Finally, historical techniques tend to output complex information that can only be interpreted and understood by professionals, making the use of this technology limited.

BRIEF SUMMARY

Although extensive gait analysis is a potentially groundbreaking technology that can enhance recovery and prevent injury for anyone that is training, it is utilized sparingly by only those that can afford it. Understanding biomechanics during training to prevent injury may help hundreds of thousands each year avoid pain and suffering and may also help reduce significant costs currently plaguing the health care system.

Accordingly, to surmount these problems, embodiments of a sensor assembly are described that are configured to provide motion data of various body segments for the purpose of facilitating enhanced user training and recovery decisions. The sensor assembly comprises a first surface comprising an adhesive material and configured to attach to a user, a second surface comprising a flexible printed circuit board (PCB) with a flexible housing mounted with electronic components, a positioning indicator configured to aid in the proper placement of the sensor assembly on a user, a first sensor supported on the PCB and configured to track motion of certain body segments of a user, and a second sensor supported on the PCB and configured to track motion of certain body segments of a user. The sensor assembly may be configured such that the distance between the first and second sensors is known. Moreover, the sensor assembly may be configured such that the first and second sensors are electrically connected to the PCB and are configured to enable the storage and transfer of the motion data.

In some embodiments, the first sensor and the second sensor of the sensor assembly are inertial sensors. For example, the first sensor and the second sensor may be 9-axis inertial sensors. Additionally or alternatively, the sensor assembly may further comprise a single sensor configured to be worn directly on or around a particular body segment.

In some cases, the flexible printed circuit board may be curved for intuitive alignment around a user's joints and body segments. Moreover, the sensor assembly may include an indication of preferred placement location on a user by utilizing an assembly that is colored and/or an assembly that is textured. Additionally, the sensor assembly may comprise an adhesive material that is a temporary bonding surface such that the assembly is removed after testing is completed.

In other embodiments, a method of tracking motion of certain body segments of a user may be provided, where the sensor assembly is configured to provide motion data of various body segments. The method may comprise receiving data from a sensor assembly attached to a user. The sensor assembly comprises a first surface comprising an adhesive material and configured to attach to a user, a second surface comprising a flexible printed circuit board (PCB) with a flexible housing mounted with electronic components, a positioning indicator configured to aid in the proper placement of the sensor assembly on a user, a first sensor supported on the PCB and configured to track motion of certain body segments of a user, and a second sensor supported on the PCB and configured to track motion of certain body segments of a user. The method further comprises configuring the sensor assembly such that the distance between the first and second sensors is known, configuring the sensor assembly such that the first and second sensors are electrically connected to the PCB, and configuring the sensor assembly to enable the storage and transfer of the motion data. The method further comprises determining a location of placement upon the user, the location being detected using an inertial frame reference calculated by determining inertial differentials between the two sensors, and tracking changes in the position of a user's certain body segments in three-dimensional space during motion to output a motion data.

In some cases, the method may comprise recording motion data, wherein motion data is recorded upon at least one of a manual starting process and a detection of motion. Additionally, the method may comprise limiting the functionality of the sensing device upon reaching a point of low power.

In some embodiments, the method may further comprise saving the motion data for long-term storage upon tracking the motion. Moreover, the motion data may be live-streamed upon tracking the motion. The method may further comprise altering the sensing device sensitivity upon selecting between various user profiles.

In other embodiments, an apparatus comprising at least one processor and at least one memory including computer program code, the at least one memory and the computer program code configured to, with the processor, cause the apparatus to at least track motion of certain body segments of a user. The apparatus, wherein the at least one memory and the computer program code are further configured to, with the processor, may cause the apparatus to receive data from a sensor assembly attached to a user. The sensor assembly comprises a first surface comprising an adhesive material and configured to attach to a user, a second surface comprising a flexible printed circuit board (PCB) with a flexible housing mounted with electronic components, a positioning indicator configured to aid in the proper placement of the sensor assembly on a user, a first sensor supported on the PCB and configured to track motion of certain body segments of a user, and a second sensor supported on the PCB and configured to track motion of certain body segments of a user. The apparatus is further configured such that the distance between the first and second sensors is known, the first and second sensors are electrically connected to the PCB, and storage and transfer of motion data is enabled. The apparatus is further configured to determine a location of placement upon the user, the location being detected using an inertial frame reference calculated by determining inertial differentials between the two sensors. Moreover, the apparatus tracks changes in the position of a user's certain body segments in three-dimensional space during motion to output a motion data.

In some cases, the apparatus, wherein the at least one memory and the computer program code are further configured to, with the processor, may cause the apparatus to record motion data, wherein motion data is recorded upon at least one of a manual starting process and a detection of motion. Additionally, the apparatus may limit the functionality of the sensing device upon reaching a point of low power.

In some embodiments, the apparatus may save the motion data for long-term storage upon tracking the motion and the motion data may be live-streamed upon tracking the motion. The apparatus may further alter the sensing device sensitivity upon selecting between various user profiles.

In other embodiments, a computer program product comprising at least one non-transitory computer-readable store medium having computer-executable program code instructions stored therein, the computer-executable program code instructions comprising program code instructions for: tracking motion of certain body segments of a user where the sensor assembly is configured to provide biomechanics based on motion. The computer-executable program instructions may comprise program code instructions for receiving data from a sensor assembly attached to a user. The sensor assembly comprises a first surface comprising an adhesive material and is configured to attach to a user, a second surface comprising a flexible printed circuit board (PCB) with a flexible housing mounted with electronic components, a positioning indicator configured to aid in the proper placement of the sensor assembly on a user, a first sensor supported on the PCB and configured to track motion of certain body segments of a user, and a second sensor supported on the PCB and configured to track motion of certain body segments of a user. The computer-executable program instructions may comprise program code instructions for configuring the sensor assembly such that the distance between the first and second sensors is known, configuring the sensor assembly such that the first and second sensors are electrically connected to the PCB, and configuring the sensor assembly to enable the storage and transfer of the motion data. The computer-executable program instructions may comprise program code instructions for determining a location of placement upon the user, the location being detected using an inertial frame reference calculated by determining inertial differentials between the two sensors, and tracking changes in the position of a user's certain body segments in three-dimensional space during motion to output a motion data.

In some cases, the computer-executable program instructions may comprise program code instructions for recording motion data, wherein motion data is recorded upon at least one of a manual starting process and a detection of motion. Additionally, the computer-executable program instructions may comprise program code instructions for limiting the functionality of the sensing device upon reaching a point of low power. In some embodiments, the computer-executable program instructions may comprise program code instructions for saving the motion data for long-term storage upon tracking the motion, and/or live-streaming the motion data upon tracking the motion. The computer-executable program instructions may comprise program code instructions for altering the sensing device sensitivity upon selecting between various user profiles.

In other embodiments, a method of analyzing motion data derived from inertial sensors using an intelligent device may be provided. The method may comprise receiving raw three-dimensional motion data at the intelligent device and processing the raw three-dimensional data into translatable data points, wherein the processing may comprise cleaning the data to eliminate noise, detecting cycles in the data and isolating these cycles, detecting motion features in the data comprising pronation, hip-drop, stride length, foot strike, hip tilt, hip rotation, and toe rotation, detecting form features in the data, and performing single and double integrations on the data. Additionally or alternatively, the method of analyzing motion data may comprise deriving specified metrics from the processed data comprising stride length, impact force, pace, and cadence, outputting processed data back to the sensing device and/or the user, and uploading the processed data to a server.

In some embodiments, the method may further comprise receiving three-dimensional data by at least one of: live-streaming the data and uploading the data at a later time. Additionally, the method may comprise sending data back to the intelligent device for further processing after being uploaded to the server. The method may further comprise initiating cues, alerts, or other communications with the user upon recognition of specified metrics or motion features, wherein the cues, alerts, or other communications are set by at least one of: manually set by the user or automated by the intelligent device. Additionally or alternatively, the method may comprise initiating communication with the user, wherein initiating communication with the user utilizes at least one of: patterns, thresholds, and sequences within the specified metrics or motion features as determined by the intelligent device or set by the user.

In some cases, the method may further comprise comparing multiple sets of data, wherein the comparing of multiple sets of data comprises at least one of: a single user comparing an historical data set to a current data set, a comparison between multiple users, and a comparison between a single user's data set to an ideal form. Moreover, the method may further comprise highlighting the results of the gait analysis via a simple visual interface.

In other embodiments, an apparatus comprising at least one processor and at least one memory including computer program code, the at least one memory and the computer program code configured to, with the processor, cause the apparatus to at least analyze motion data derived from inertial sensors using an intelligent device. The apparatus, wherein the at least one memory and the computer program code are further configured to, with the processor, cause the apparatus to receive raw three-dimensional motion data at the intelligent device and process the raw three-dimensional data into translatable data points, wherein the processing may comprise cleaning the data to eliminate noise, detecting cycles in the data and isolating these cycles, detecting motion features in the data comprising pronation, hip-drop, stride length, foot strike, hip tilt, hip rotation, and toe rotation, detecting form features in the data, and performing single and double integrations on the data. Additionally or alternatively, the apparatus may derive specified metrics from the processed data comprising stride length, impact force, pace, and cadence, output processed data back to the sensing device and/or the user, and upload the processed data to a server.

In some embodiments, the apparatus may receive three-dimensional data by at least one of: live-streaming the data and uploading the data at a later time. Additionally, the apparatus may send data back to the intelligent device for further processing after being uploaded to the server. The apparatus may further initiate cues, alerts, or other communications with the user upon recognition of specified metrics or motion features, wherein the cues, alerts, or other communications are set by at least one of: manually set by the user or automated by the intelligent device. Additionally or alternatively, the apparatus, wherein the at least one memory and the computer program code are further configured to, with the processor, may cause the apparatus to initiate communication with the user, wherein initiating communication with the user utilizes at least one of: patterns, thresholds, and sequences within the specified metrics or motion features as determined by the intelligent device or set by the user.

In some cases, the apparatus may compare multiple sets of data, wherein the comparing of multiple sets of data comprises at least one of: a comparison of a single user's historical data set to a current data set, a comparison between multiple users, and a comparison between a single user's data set to an ideal form. Moreover, the apparatus may further highlight the results of the gait analysis via a simple visual interface.

In other embodiments, a computer program product comprising at least one non-transitory computer-readable storage medium having computer-executable program code instructions stored therein, the computer-executable program code instructions comprising program code instructions for analyzing motion data derived from inertial sensors using an intelligent device may be provided. The computer-executable program code instructions further comprise program code instructions for receiving raw three-dimensional motion data at the intelligent device and processing the raw three-dimensional data into translatable data points, wherein the processing may comprise cleaning the data to eliminate noise, detecting cycles in the data and isolating these cycles, detecting motion features in the data comprising pronation, hip-drop, stride length, foot strike, hip tilt, hip rotation, and toe rotation, detecting form features in the data, and performing single and double integrations on the data. Additionally or alternatively, the computer-executable program code instructions further comprise program code instructions for analyzing motion data may comprise deriving specified metrics from the processed data comprising stride length, impact force, pace, and cadence, outputting processed data back to the sensing device and/or the user, and uploading the processed data to a server.

In some embodiments, the computer-executable program code instructions further comprise program code instructions for receiving three-dimensional data by at least one of: live-streaming the data and uploading the data at a later time. Additionally, the computer program product may comprise sending data back to the intelligent device for further processing after being uploaded to the server. The computer-executable program code instructions further comprise program code instructions for initiating cues, alerts, or other communications with the user upon recognition of specified metrics or motion features, wherein the cues, alerts, or other communications are set by at least one of: manually set by the user or automated by the intelligent device. Additionally or alternatively, the computer-executable program code instructions further comprise program code instructions for initiating communication with the user, wherein initiating communication with the user utilizes at least one of: patterns, thresholds, and sequences within the specified metrics or motion features as determined by the intelligent device or set by the user.

In some cases, the computer-executable program code instructions further comprise program code instructions for comparing multiple sets of data, wherein the comparing of multiple sets of data comprises at least one of: a single user comparing an historical data set to a current data set, a comparison between multiple users, and a comparison between a single user's data set to an ideal form. Moreover, the computer program may further comprise highlighting the results of the gait analysis via a simple visual interface.

In still other embodiments, a system is provided for tracking motion of certain body segments of a user, the system comprising a sensor assembly configured to track motion, and an apparatus comprising at least one processor and at least one memory including computer program code, the at least one memory and the computer program code configured to, with the processor, cause the apparatus to at least track motion of certain body segments of a user.

The sensor assembly comprises a first surface comprising an adhesive material and configured to attach to a user, a second surface comprising a flexible printed circuit board (PCB) with a flexible housing mounted with electronic components, a positioning indicator configured to aid in the proper placement of the sensor assembly on a user, a first sensor supported on the PCB and configured to track motion of certain body segments of a user, and a second sensor supported on the PCB and configured to track motion of certain body segments of a user. The sensor assembly may be configured such that the distance between the first and second sensors is known. Moreover, the sensor assembly may be configured such that the first and second sensors are electrically connected to the PCB and are configured to enable the storage and transfer of the motion data.

In some embodiments, the first sensor and the second sensor of the sensor assembly are inertial sensors. For example, the first sensor and the second sensor may be 9-axis inertial sensors. Additionally or alternatively, the sensor assembly may further comprise a single sensor configured to be worn directly on or around a particular body segment.

In some cases, the flexible printed circuit board may be curved for intuitive alignment around a user's joints and body segments. Moreover, the sensor assembly may include an indication of preferred placement location on a user by utilizing an assembly that is colored and/or an assembly that is textured. Additionally, the sensor assembly may comprise an adhesive material that is a temporary bonding surface such that the assembly is removed after testing is completed.

The apparatus, wherein the at least one memory and the computer program code are further configured to, with the processor, may cause the apparatus to receive data from a sensor assembly attached to a user. The apparatus is further configured to determine a location of placement upon the user, the location being detected using an inertial frame reference calculated by determining inertial differentials between the two sensors. Moreover, the apparatus tracks changes in the position of a user's certain body segments in three-dimensional space during motion to output a motion data.

In some cases, the apparatus, wherein the at least one memory and the computer program code are further configured to, with the processor, may cause the apparatus to record motion data, wherein motion data is recorded upon at least one of a manual starting process and a detection of motion. Additionally, the apparatus may limit the functionality of the sensing device upon reaching a point of low power.

In some embodiments, the apparatus may save the motion data for long-term storage upon tracking the motion and the motion data may be live-streamed upon tracking the motion. The apparatus may further alter the sensing device sensitivity upon selecting between various user profiles.

In still other embodiments, a system is provided for analyzing motion data of certain body segments, the system comprising a sensor assembly configured to track motion, and an apparatus comprising at least one processor and at least one memory including computer program code, the at least one memory and the computer program code configured to, with the processor, cause the apparatus to at least analyze motion data derived from the sensor assembly using an intelligent device.

The sensor assembly comprises a first surface comprising an adhesive material and configured to attach to a user, a second surface comprising a flexible printed circuit board (PCB) with a flexible housing mounted with electronic components, a positioning indicator configured to aid in the proper placement of the sensor assembly on a user, a first sensor supported on the PCB and configured to track motion of certain body segments of a user, and a second sensor supported on the PCB and configured to track motion of certain body segments of a user. The sensor assembly may be configured such that the distance between the first and second sensors is known. Moreover, the sensor assembly may be configured such that the first and second sensors are electrically connected to the PCB and are configured to enable the storage and transfer of the motion data.

In some embodiments, the first sensor and the second sensor of the sensor assembly are inertial sensors. For example, the first sensor and the second sensor may be 9-axis inertial sensors. Additionally or alternatively, the sensor assembly may further comprise a single sensor configured to be worn directly on or around a particular body segment.

In some cases, the flexible printed circuit board may be curved for intuitive alignment around a user's joints and body segments. Moreover, the sensor assembly may include an indication of preferred placement location on a user by utilizing an assembly that is colored and/or an assembly that is textured. Additionally, the sensor assembly may comprise an adhesive material that is a temporary bonding surface such that the assembly is removed after testing is completed.

The apparatus, wherein the at least one memory and the computer program code are further configured to, with the processor, cause the apparatus to receive raw three-dimensional motion data at the intelligent device and process the raw three-dimensional data into translatable data points, wherein the processing may comprise cleaning the data to eliminate noise, detecting cycles in the data and isolating these cycles, detecting motion features in the data comprising pronation, hip-drop, stride length, foot strike, hip tilt, hip rotation, and toe rotation, detecting form features in the data, and performing single and double integrations on the data. Additionally or alternatively, the apparatus may derive specified metrics from the processed data comprising stride length, impact force, pace, and cadence, output processed data back to the sensing device and/or the user, and upload the processed data to a server.

In some embodiments, the apparatus may receive three-dimensional data by at least one of: live-streaming the data and uploading the data at a later time. Additionally, the apparatus may send data back to the intelligent device for further processing after being uploaded to the server. The apparatus may further initiate cues, alerts, or other communications with the user upon recognition of specified metrics or motion features, wherein the cues, alerts, or other communications are set by at least one of: manually set by the user or automated by the intelligent device. Additionally or alternatively, the apparatus, wherein the at least one memory and the computer program code are further configured to, with the processor, may cause the apparatus to initiate communication with the user, wherein initiating communication with the user utilizes at least one of: patterns, thresholds, and sequences within the specified metrics or motion features as determined by the intelligent device or set by the user.

In some cases, the apparatus may compare multiple sets of data, wherein the comparing of multiple sets of data comprises at least one of: a comparison of a single user's historical data set to a current data set, a comparison between multiple users, and a comparison between a single user's data set to an ideal form. Moreover, the apparatus may further highlight the results of the gait analysis via a simple visual interface.

In still other embodiments, a system is provided for tracking and subsequently analyzing motion of certain body segments of a user, the system comprising a sensor assembly configured to track motion, an apparatus comprising at least one processor and at least one memory including computer program code, the at least one memory and the computer program code configured to, with the processor, cause the apparatus to at least track motion of certain body segments of a user, and an apparatus comprising at least one processor and at least one memory including computer program code, the at least one memory and the computer program code configured to, with the processor, cause the apparatus to at least analyze motion data derived from the sensor assembly using an intelligent device.

The sensor assembly comprises a first surface comprising an adhesive material and configured to attach to a user, a second surface comprising a flexible printed circuit board (PCB) with a flexible housing mounted with electronic components, a positioning indicator configured to aid in the proper placement of the sensor assembly on a user, a first sensor supported on the PCB and configured to track motion of certain body segments of a user, and a second sensor supported on the PCB and configured to track motion of certain body segments of a user. The sensor assembly may be configured such that the distance between the first and second sensors is known. Moreover, the sensor assembly may be configured such that the first and second sensors are electrically connected to the PCB and are configured to enable the storage and transfer of the motion data.

In some embodiments, the first sensor and the second sensor of the sensor assembly are inertial sensors. For example, the first sensor and the second sensor may be 9-axis inertial sensors. Additionally or alternatively, the sensor assembly may further comprise a single sensor configured to be worn directly on or around a particular body segment.

In some cases, the flexible printed circuit board may be curved for intuitive alignment around a user's joints and body segments. Moreover, the sensor assembly may include an indication of preferred placement location on a user by utilizing an assembly that is colored and/or an assembly that is textured. Additionally, the sensor assembly may comprise an adhesive material that is a temporary bonding surface such that the assembly is removed after testing is completed.

The apparatus, wherein the at least one memory and the computer program code are further configured to, with the processor, may cause the apparatus to receive data from a sensor assembly attached to a user. The apparatus is further configured to determine a location of placement upon the user, the location being detected using an inertial frame reference calculated by determining inertial differentials between the two sensors. Moreover, the apparatus tracks changes in the position of a user's certain body segments in three-dimensional space during motion to output a motion data.

In some cases, the apparatus, wherein the at least one memory and the computer program code are further configured to, with the processor, may cause the apparatus to record motion data, wherein motion data is recorded upon at least one of a manual starting process and a detection of motion. Additionally, the apparatus may limit the functionality of the sensing device upon reaching a point of low power.

In some embodiments, the apparatus may save the motion data for long-term storage upon tracking the motion and the motion data may be live-streamed upon tracking the motion. The apparatus may further alter the sensing device sensitivity upon selecting between various user profiles.

The apparatus, wherein the at least one memory and the computer program code are further configured to, with the processor, cause the apparatus to receive raw three-dimensional motion data at the intelligent device and process the raw three-dimensional data into translatable data points, wherein the processing may comprise cleaning the data to eliminate noise, detecting cycles in the data and isolating these cycles, detecting motion features in the data comprising pronation, hip-drop, stride length, foot strike, hip tilt, hip rotation, and toe rotation, detecting form features in the data, and performing single and double integrations on the data. Additionally or alternatively, the apparatus may derive specified metrics from the processed data comprising stride length, impact force, pace, and cadence, output processed data back to the sensing device and/or the user, and upload the processed data to a server.

In some embodiments, the apparatus may receive three-dimensional data by at least one of: live-streaming the data and uploading the data at a later time. Additionally, the apparatus may send data back to the intelligent device for further processing after being uploaded to the server. The apparatus may further initiate cues, alerts, or other communications with the user upon recognition of specified metrics or motion features, wherein the cues, alerts, or other communications are set by at least one of: manually set by the user or automated by the intelligent device. Additionally or alternatively, the apparatus, wherein the at least one memory and the computer program code are further configured to, with the processor, may cause the apparatus to initiate communication with the user, wherein initiating communication with the user utilizes at least one of: patterns, thresholds, and sequences within the specified metrics or motion features as determined by the intelligent device or set by the user.

In some cases, the apparatus may compare multiple sets of data, wherein the comparing of multiple sets of data comprises at least one of: a comparison of a single user's historical data set to a current data set, a comparison between multiple users, and a comparison between a single user's data set to an ideal form. Moreover, the apparatus may further highlight the results of the gait analysis via a simple visual interface.

Example embodiments of the present invention enhance the user experience by enabling self-identification of various gait patterns. Enhanced user self-sufficiency allows this technology to be more readily used by the general population. In addition, due to the augmented functionality that increases the accuracy of the biomechanical analysis, example embodiments of the present invention provide a way to more precisely make training and recovery decisions that may significantly impact one's well-being.

BRIEF DESCRIPTION OF THE DRAWINGS

Features will become apparent to those of skill in the art by describing in detail exemplary embodiments with reference to the attached drawings in which.

DETAILED DESCRIPTION

Figure 1:
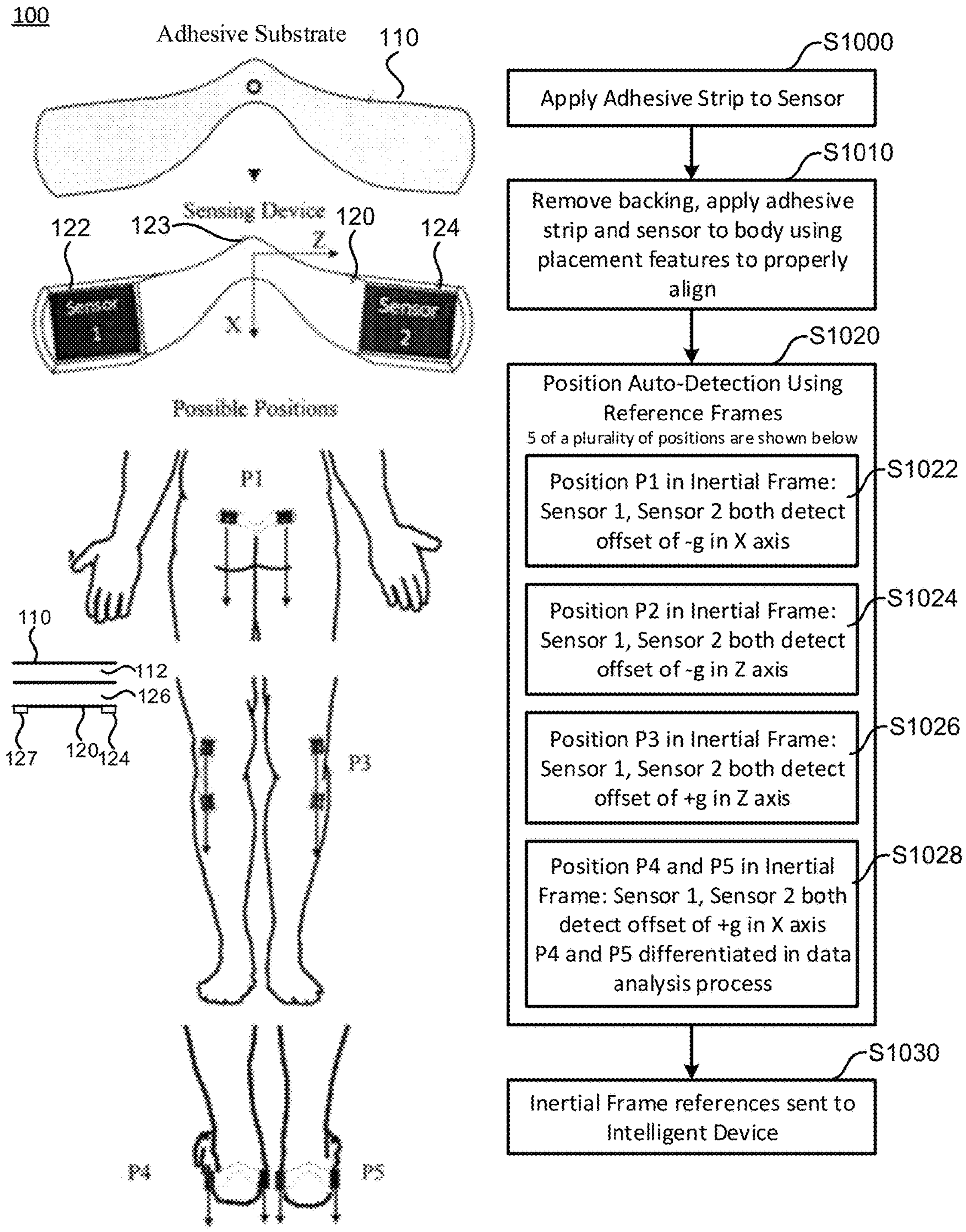
FIG. 1 illustrates a binodal sensing device in accordance with an embodiment, various positions at which it may be attached, and a flowchart of an associated method.

Example embodiments will now be described more fully hereinafter with reference to the accompanying drawings;

however, they may be embodied in different forms and should not be construed as limited to the embodiments set forth herein. Rather, these embodiments are provided so that this disclosure will be thorough and complete, and will fully convey exemplary implementations to those skilled in the art.

Detailed descriptions of commonly-used technologies related to the disclosure that may obscure embodiments may be omitted. In addition, though terms like a first and a second are used to describe various components, the components should not be limited by the terms. The terms may be used for the purpose of distinguishing one component from another.

In the drawing figures, the dimensions of layers and regions may be exaggerated for clarity of illustration. In particular, the relative dimensions of the accompanying drawings may not be drawn to scale unless specifically identified as a scaled representational drawing. It will also be understood that when a layer or element is referred to as being “on” another layer or element, it can be directly on the other layer or element, or intervening layers or elements may also be present. Further, it will be understood that when a layer is referred to as being “under” another layer, it can be directly under, and one or more intervening layers may also be present. In addition, it will also be understood that when a layer is referred to as being “between” two layers, it can be the only layer between the two layers, or one or more intervening layers may Details of the implementation, aspects, and features of two or more implementations described herein are set forth with representational drawings and accompanying descriptions to follow.

OVERVIEW

A method and apparatus are provided in accordance with an example embodiment of the present invention to track movement using wearable sensors to improve the ability to analyze gait during recovery and training.

One embodiment of the present invention is directed to a binodal sensing device. The binodal sensing device is configured to attach to a user and determine various metrics of the user’s gait, technique, or other movement. The binodal sensing device is made up of at least two inertial sensors, a first sensor and a second sensor, which may be placed on the body to determine certain metrics of particular body segments. This construction may be adhesively attached to the body and include a flexible printed circuit board (PCB) on which the sensors are mounted to minimize intrusiveness to the user. Features to aid in proper placement of the device on the user’s body may also be included. These features allow an unskilled person to place the sensor construction for gait analysis.

Figure 7:
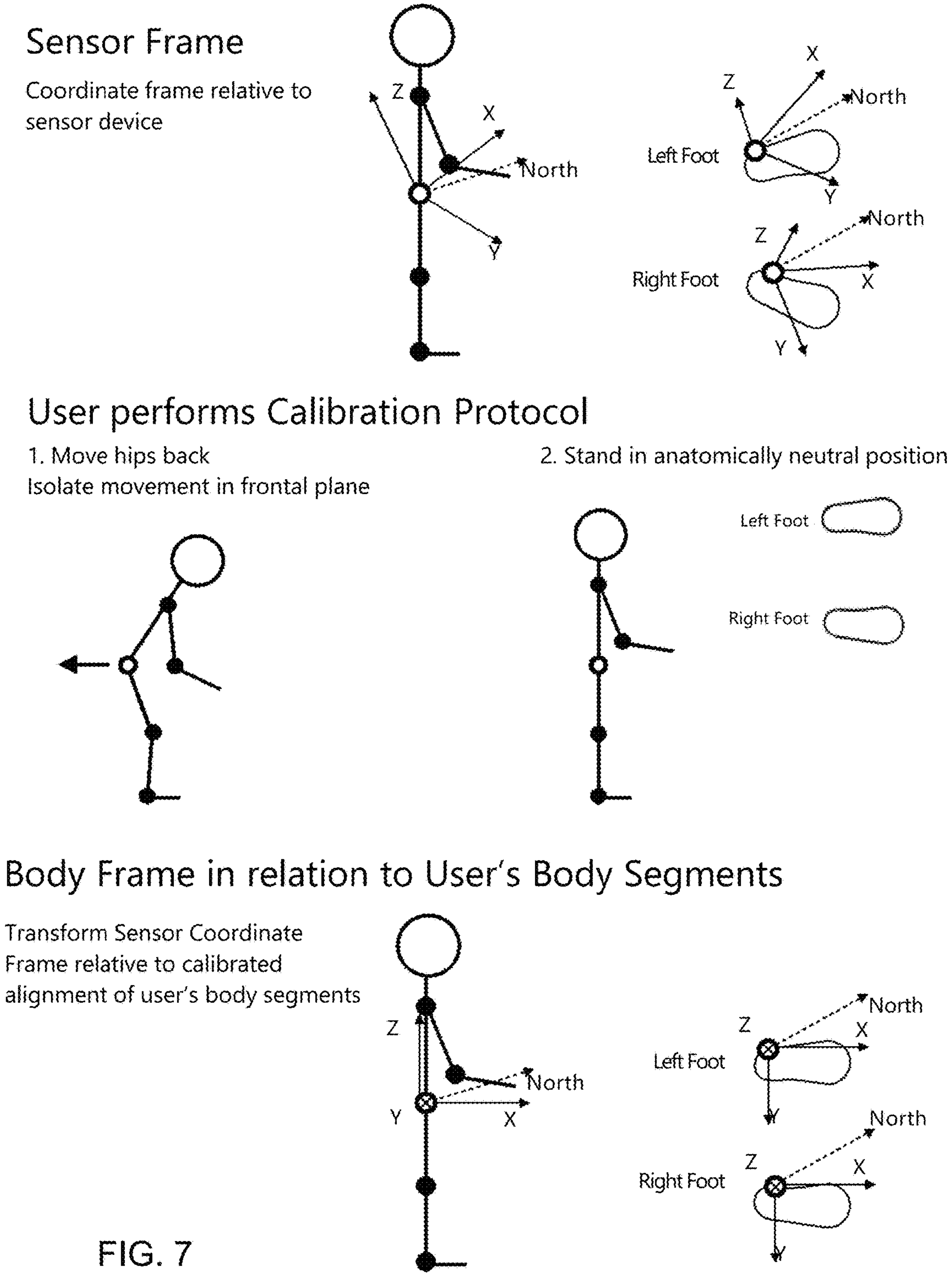
FIG. 7 illustrates automatically determining placement of the sensor on the body via the use of an absolute reference frame and forward movement and/or a set of calibration movements or positions performed by the wearer.

Another embodiment of the present invention is a method for modeling and tracking motion. The binodal sensing device, among other things, (1) renders metrics of internal stability or torsion for a segment, (2) renders metrics of position or motion between two segments, and (3) improves the accuracy of rectilinear acceleration and angular gyro values of a single segment. Once attached, the binodal sensing device may automatically determine its placement on the body via the use of an absolute reference frame and forward movement and/or a set of calibration movements or positions performed by the wearer as illustrated in FIG. 7. Once the placement has been calculated, the changing position of the sensing device may be detected via reference frames.

Another embodiment is directed to a method for analyzing athletic performance and performing injury risk analysis. The data detected by the sensor is sent to an intelligent device that can be any user-friendly smart device. This data transfer may be done in real-time via live-streaming or may be uploaded at a later time directly to the intelligent device. Profiles for specific users may be generated to create customized settings for the sensing device and to store historical data for future reference and analysis. Data received by the intelligent device can be appropriately processed to determine various motion features, including, among other things, stride length, impact force, pace, pronation, hip-drop, foot strike, hip tilt and rotation, and toe rotation. Historical data from the specified user or data from other users, including data representing ideal metrics, may be compared to test results. Differences in test results can be analyzed by the intelligent device and indicated so that any user may determine where gait metrics may need improvement. Furthermore, the intelligent device may provide real-time feedback and coaching to aid in matching a desired gait.

A binodal, wearable, e.g., skin-adhered, or otherwise secured to a user, flexible sensing device (SD) for monitoring biomechanics, form, and associated biometrics functions and methods of an associate platform are described below.

As illustrated in FIG. 1.*a*, an SD 100 may include a first bonding surface 110 and a second surface 120, opposite the first bonding surface 110, on which a first sensor 122 and a second sensor 124 are mounted. The first and second sensors 122, 124 are inertial sensors, e.g., 9-axis inertial sensors, and may be the same as one another. The first and second sensors 122, 124 may combine to determine 9-axis inertial measurement units. These nodes are optimized to reduce signal-to-noise-ratio by minimizing the relative motion of the device to the wearer’s body via location on bony segments and the minimization of sensor inertia; thickness (<6 mm) and weight (<10 g) per node, or other mechanical means such as firm conformity to the skin.

Figure 8:
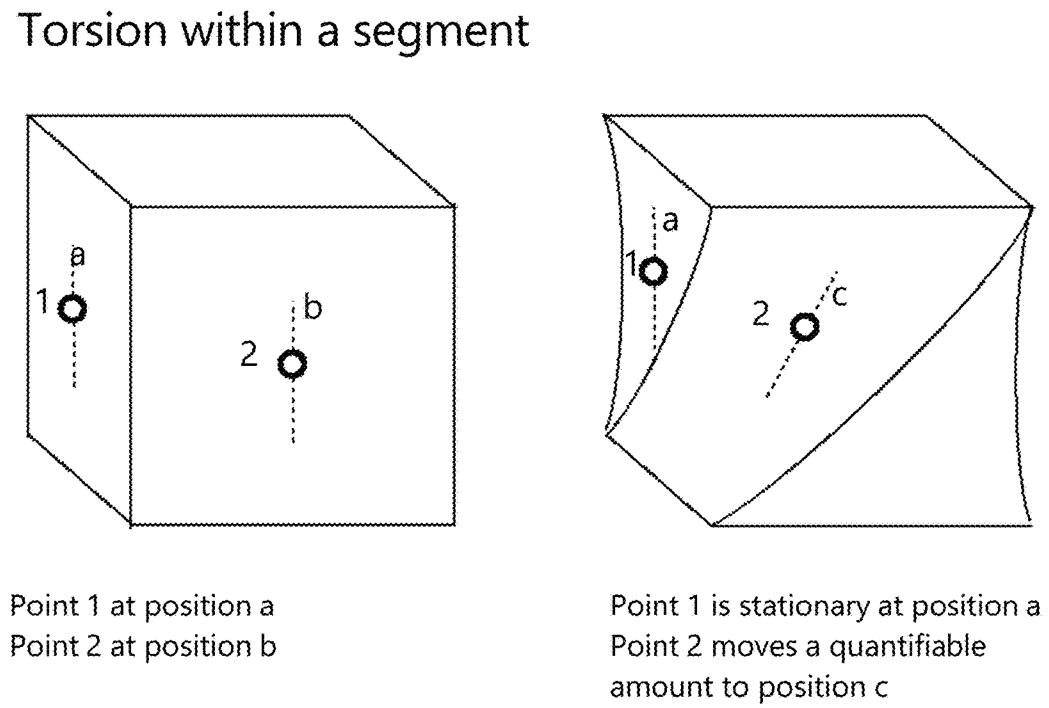
FIG. 8 illustrates the use of two sensors to render metrics of internal stability or torsion for a segment.
Figure 9:
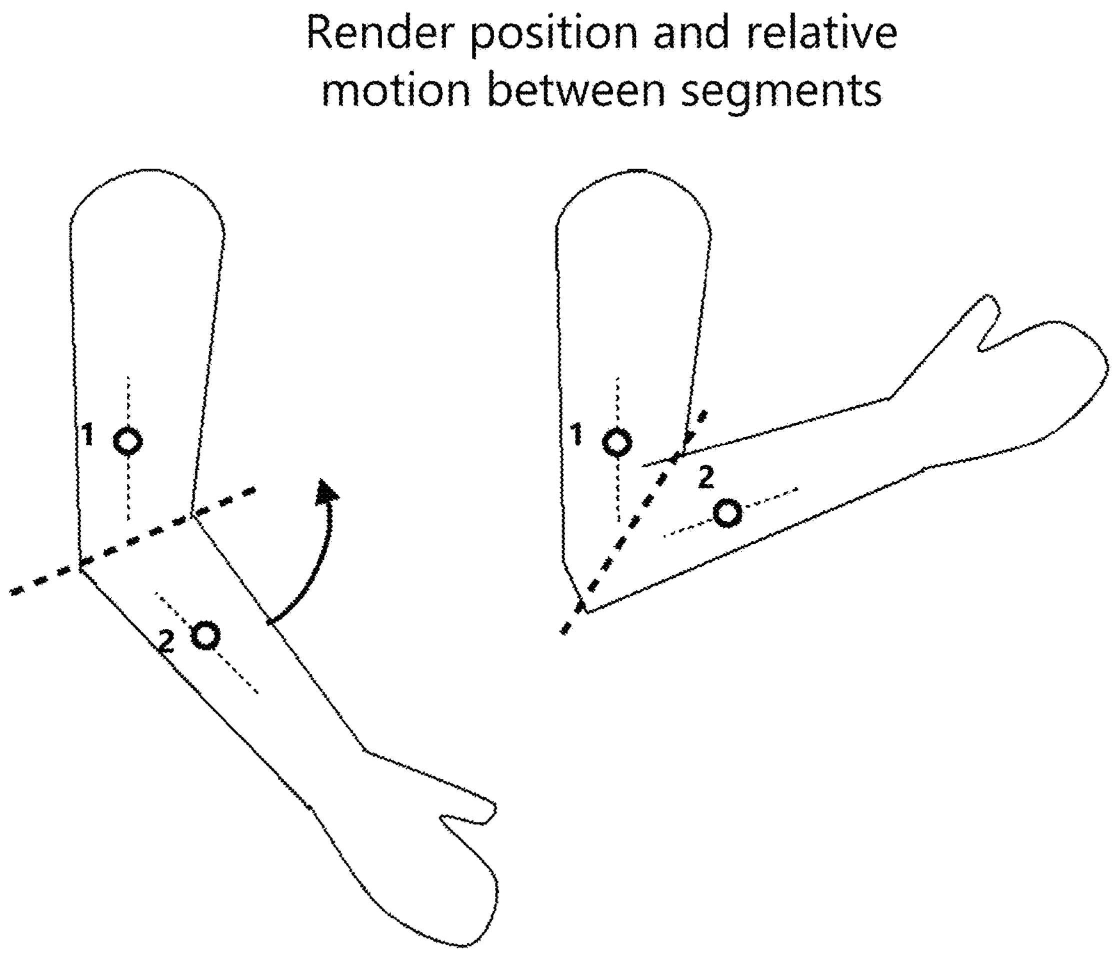
FIG. 9 illustrates the use of two sensors to render metrics of position or relative motion between two segments.

The second surface 120 may include a flexible printed circuit board (PCB) 126 on which the first and second sensors 122, 124 are mounted. The PCB may be rigid or the electronics may just be connected by wire. The flexible PCB includes electronic components of a nominal maximum thickness and length to minimize potential noise and general intrusiveness of the device to the user. The sensors 122, 124 may be separated by a known gap g along a plane of the SD 100 (this distance d is along either the X or A axis, depending upon placement of the SD, discussed in detail below). The use of two sensors 122, 124 allows the SD 100 to, among other things, (1) render metrics of internal stability or torsion for a segment such as illustrated in FIG. 8, (2) render metrics of position or relative motion between two segments such as in FIG. 9, and (3) improve the accuracy of rectilinear acceleration and angular gyro values of a single segment.

The device may be worn in direct contact with the body via the bonding surface 110, e.g., a temporary bonding surface, but may be attached to a user in other manners, e.g., outside form fitting clothing. The device may be attached to the bonding surface via an adhesive 100*a*, 112. The bonding surface 110 may be one surface of a double-sided and flexible disposable substrate 112 to adhere directly to the user’s body 100*b*. The substrate 112 may be moisture resistant to allow adherence during more strenuous activity. Substrates may include but are not limited to fabric based double sided adhesive strips like double-sided kinesio tape, silicone based adhesive strips, hydro-colloid based strips, and hook and loop fasteners (e.g., Velcro®). The other side of the substrate 112 may be adhered to the flexible PCB 100*a*, 126. Thus, the substrate 112 may be disposed of and a new substrate may be used with the flexible PCB 126. In addition to an adhesive strip 100*b*, an adhesive spray, paste, gel, sticker, etc. may be used to form the bonding surface 100*c* by being directly applied to the flexible PCB 126.

A single SD 100 may be worn directly on or surrounding a body segment including but not limited to the skin of the foot, shoulder, or knee, or bridging two segments like the upper and fore arm, the lower and upper leg, shoulder and upper arm and others. The SD 100 may include features to aid in proper placement of the device on the user's body. These features may include, but are not limited to, center alignment tabs, colored or textured positioning indicators, and/or colored variation in devices.

Figure 2:
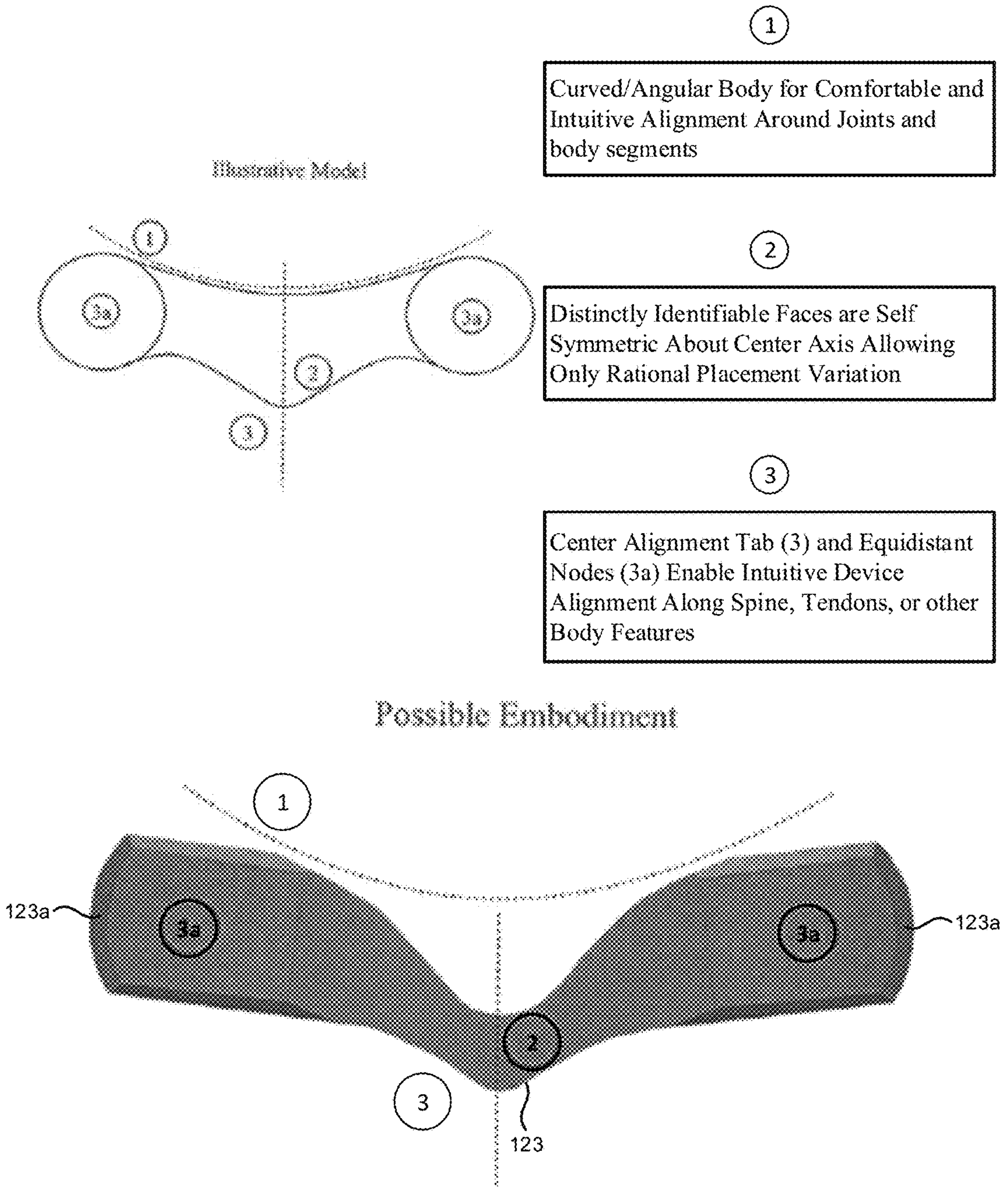
FIG. 2 illustrates schematic views of a binodal sensing device in accordance with an embodiment.

For example, as shown in detail in FIG. 2, the SD 100 may be curved for comfortable and intuitive alignment around joints and body segments. The SD 100 may be self-symmetric about a center axis to allow only rotational variation in the placement of the SD 100. The SD 100 may include a center alignment tab 123 and equidistant nodes that correspond to the sensors 122, 124 to facilitate intuitive alignment of the SD 100 on the body.

Once attached, the SD 100 may automatically determine placement on the body. For example, as illustrated in the flowchart of FIG. 1.*b*, the substrate 112 may be attached to the flexible PCB 126 (S1000), a backing on the substrate 112 may be removed and the SD 100 may be applied to the body using placement features to properly align the SD 100 (S1010). Once the SD has undergone a body frame calibration (S1010.*b*), position of the SD 100 may be detected using inertial reference frames (S1020). The SD 100 detects the device's position and orientation in space via the use of the two embedded IMU units. Using inertial sensing and inertial differentials between the two devices placement on the body may be determined. Four examples are illustrated as follows:

(1) When the SD 100 is on a back of a user, illustrated as position P1, sensors 122, 124 detect an offset of −g along the X axis (S1022);

(2) When the SD 100 is on a right knee of a user, illustrated as position P2, sensors 122, 124 detect an offset of −g along the Z axis (S1024);

(3) When the SD 100 is on a left knee of a user, illustrated as position P3, sensors 122, 124 detect an offset of +g along the Z axis (S1026); and (4) When the SD 100 is on a left heel of a user, illustrated as position P4, or on a right heel of a user, illustrated as position P5, sensors 122, 124 detect an offset of +g along the X axis knee (S1028).

The inertial frame reference detected by the sensor 122, 124 is sent to an intelligent device (ID), e.g., a smart phone, a tablet, a smart watch, a computer, and so forth, if one is being used (S1030). The reference may be provided to an ID later.

Figure 3:
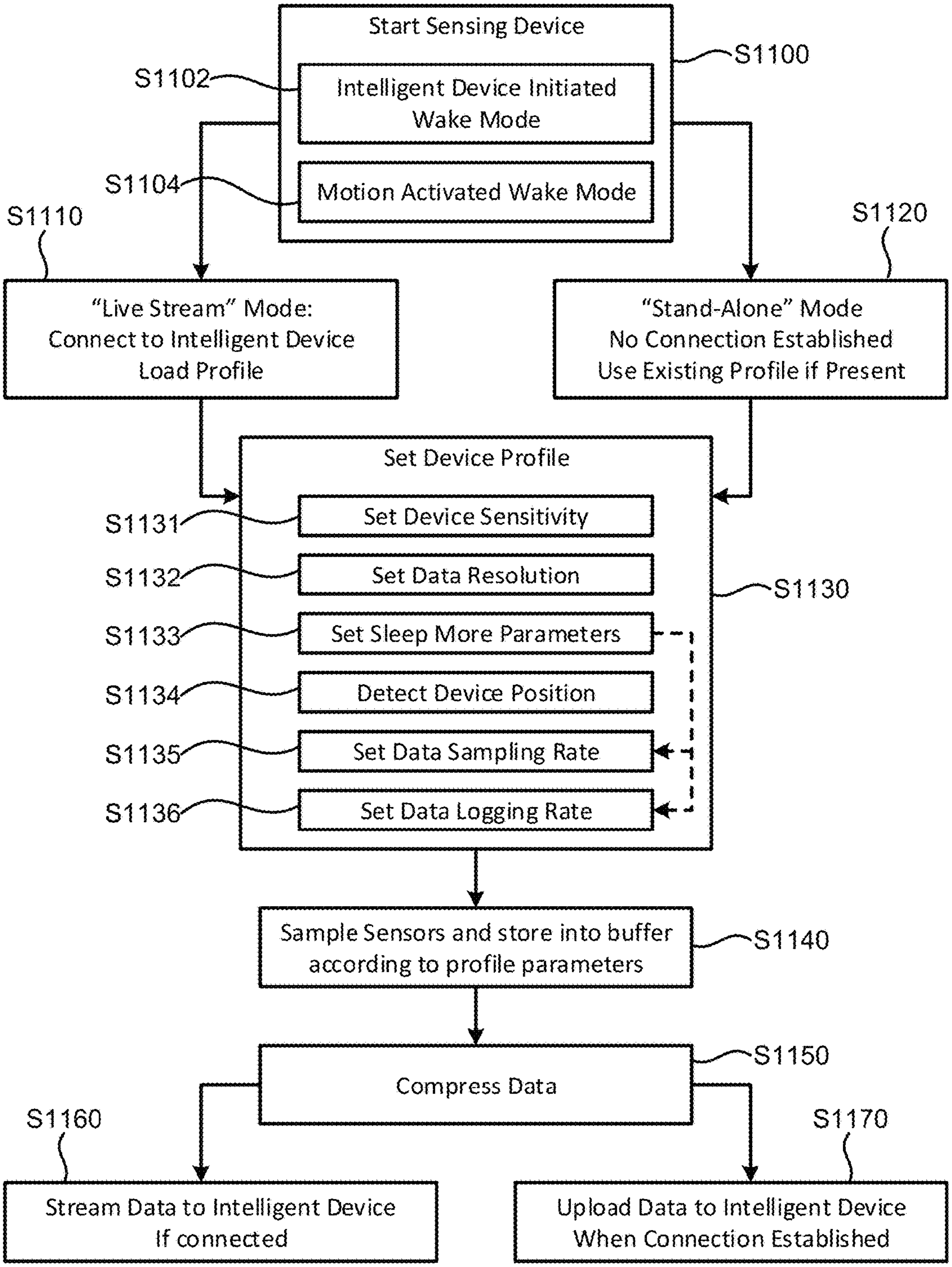
FIG. 3 illustrates a flowchart of a method of operating the binodal sensing device in accordance with an embodiment.

Operation of the SD 100 is illustrated in FIG. 3, assuming the SD 100 is in a sleep mode. First, the SD 100 is started (S1100). This start may be initiated by a wake up command from the ID (S1102), a button actuation, motion activation, or a combination of those methods (S1104). Alternatively, there may be a button to wake the SD/put the SD in sleep mode.

Once started, the SD 100 may operate in a live stream mode in which it is connected to the ID and loads the profile from the ID (S1100). If there is no ID connected, the SD 100 may operate in a stand-alone mode and use profiles sent from ID or existing profile stored in the SD 100, if available (S1120).

Then a profile of the SD 100 may be set (S1130). Setting the profile may include setting a sensor sensitivity (S1131), which, when the sensors 122, 124 are 9-axis inertial sensors, setting sensitivity (bits) for each parameter (Ax, Ay, Az, Gx, Gy, Gz, Mx, My, Mz), e.g., setting a base value for each parameter (Ax, Ay, Az, Gx, Gy, Gz, Mx, My, Mz) (S1131), setting sensitivity for each type of parameter (A vs. G), and programming the sensors 122, 124 accordingly (S1132). Setting the profile may include setting resolution (Bits) for Ax, Ay, Az, Gx, Gy, Gz, Mx, My, Mz, e.g., specifying the logging frequency, i.e. if the processor is capturing raw data from sensor at 100 hz (100 samples per second), and the resolution is 5, then every 5th data point will actually be buffered for that specific parameter (S1132). Setting the profile may include setting sleep mode parameters, e.g., idle time (how long the device is inactive before entering sleep mode) and how much change in the parameters is required to keep the SD 100 active (S1133). The sleep mode is a lower power setting which disables wireless communication, data storage, and other power intensive functions but retains sensor functionality and limited processing. The SD 100 may be put into a sleep mode when prompted by the ID, when the device is stationary or nearly stationary for a sufficient period of time, when the user is engaged in insufficient motion as per predefined parameters for a sufficient amount of time, or by a button on the SD 100. Setting the profile may include automatically detecting position of the SD 100, as illustrated in FIG. 1 (S1134). Setting the profile may include setting a data sampling rate (S1135) and a data logging rate (S1136).

Figure 10A:
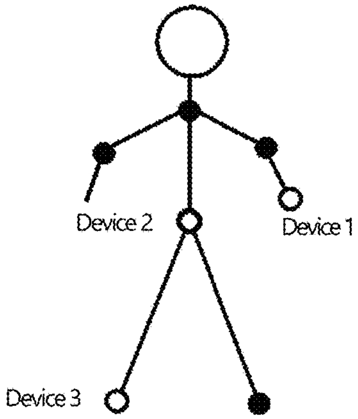
FIG. 10A illustrates how each sensor may function independently of one another in order to optimize performance for each segment location, application, sport, body type, setting, etc.
Figure 10B:
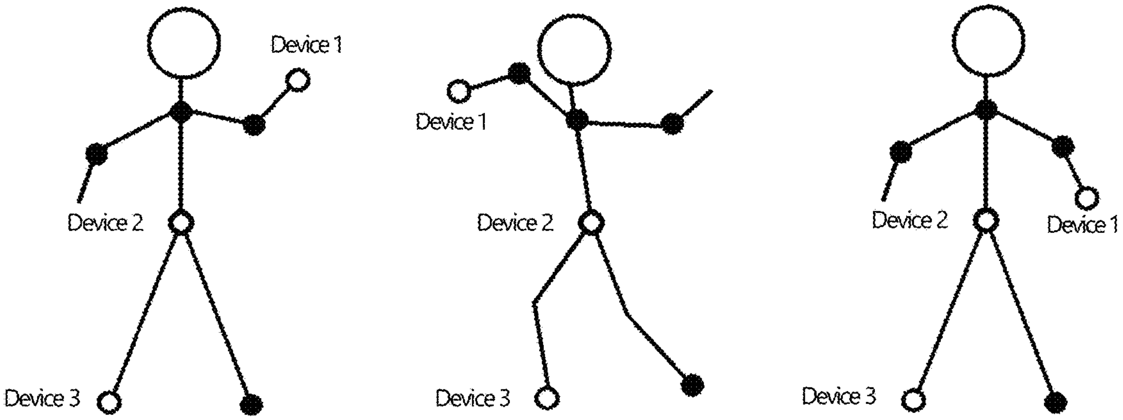
FIG. 10B illustrates how the SDs may also utilize the multiple IMU sensors contained within so simultaneously sample at different settings at the same time and/or dynamically transition between one setting to another based on the movements being performed by the athlete.

SDs may function independently of one another in order to optimize performance for each segment location, application, sport, body type, setting, etc. as illustrated in FIG. 10A. The SDs may also utilize the multiple IMU sensors contained within so simultaneously sample at different settings at the same time and/or dynamically transition between one setting to another based on the movements being performed by the athlete as in FIG. 10B.

Once the SD profile has been set, data may be retrieved from the sensors and stored, e.g., in a buffer, according the profile parameters (S1140). Then the data may be compressed, e.g., may be transferred from the buffer to long term storage while being compressed (S1150).

The compressed data may be streamed to the cloud directly via Wifi connection, to the ID if connected (S1160), e.g., using Bluetooth low energy (BLE), or may be uploaded to ID when connection established (S1170) or using a universal serial bus (USB) device.

Figure 4:
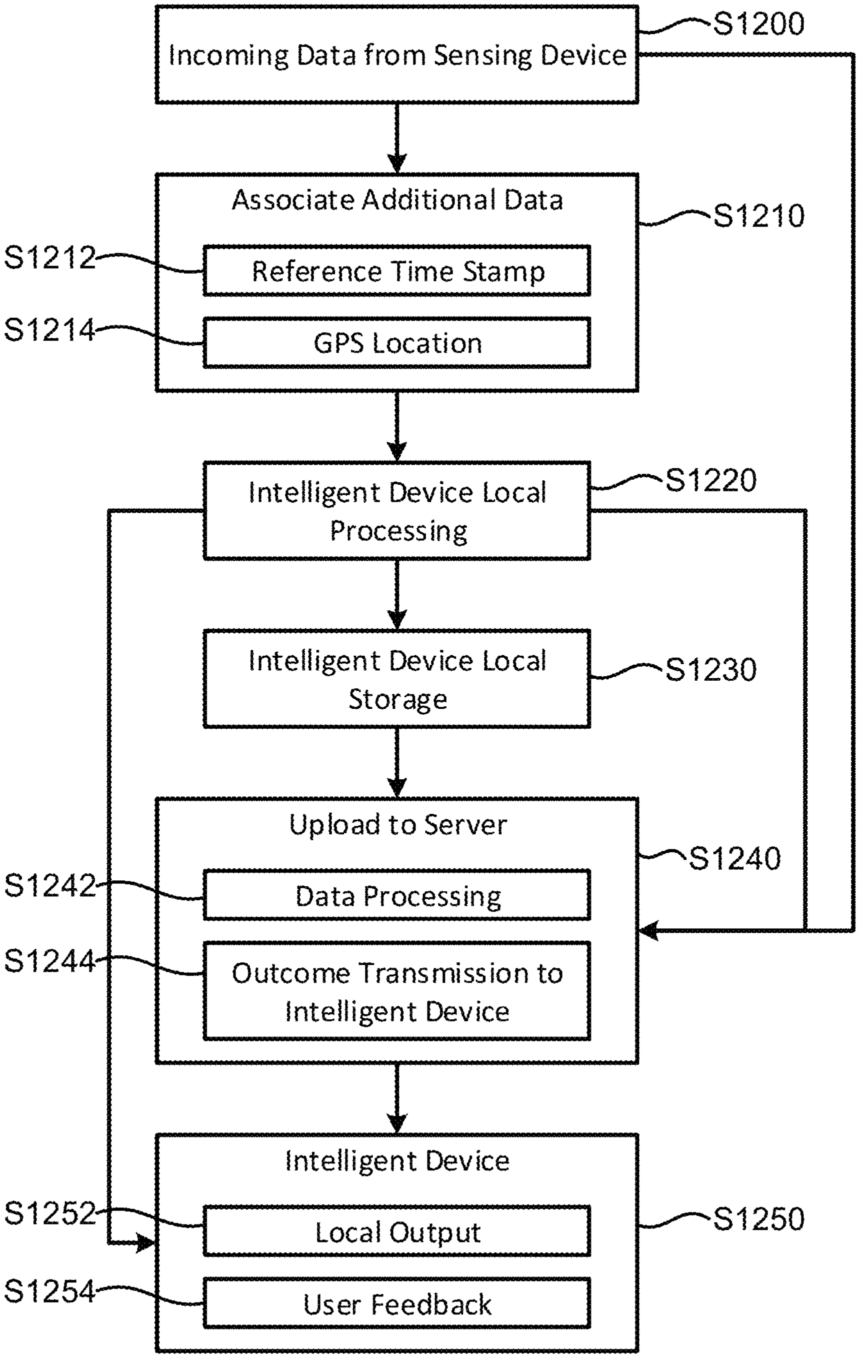
FIG. 4 illustrates a flowchart of a method of interaction between an intelligent device that has received data from the binodal sensing device and a server in accordance with an embodiment.

Possible operation on the ID side is illustrated in FIG. 4. First, incoming data is received from the SD 100 (S1200). When operating in live stream mode, the ID associates additional data, e.g., a reference time stamp (S1212), a GPS location (S1214), and so forth, with the data from the SD 100 (S1210).

The ID then does some local processing to, among other things, derive specified metrics including but not limited to stride length, impact force, pace, cadence, etc. The first step to deriving these metrics is to place the incoming data in the frame of reference of the body (Frontal, Sagittal, and Transverse). This may be done by utilizing the onboard compass as an absolute global reference and may be enhanced by prompting the user to perform a calibration movement or positions in order to coordinate a transformation matrix from the absolute, magnetic frame and the sensor frame of reference to the body frame of reference. An example is outlined in FIG. 7. This may be done on the ID, SD, or Cloud (S1220). Outputs from the ID (processed data) are then sent back to the SD 100 (S1252) and/or provides feedback to the user (S1254). The ID can then store the processed data (S1230) and/or uploads the data to a server, e.g., in the cloud (S1240), which further processes the data (disclosed below with reference to FIG. 5) (S1242) and sends the further processed data to the ID (S1244).

In the stand-alone mode, the incoming data from the SD 100 is directly uploaded to the server (S1240). The ID then outputs the server processed data back to the SD 100 (S1252) and/or provides feedback to the user (S1254) (S1250).

Figure 5:
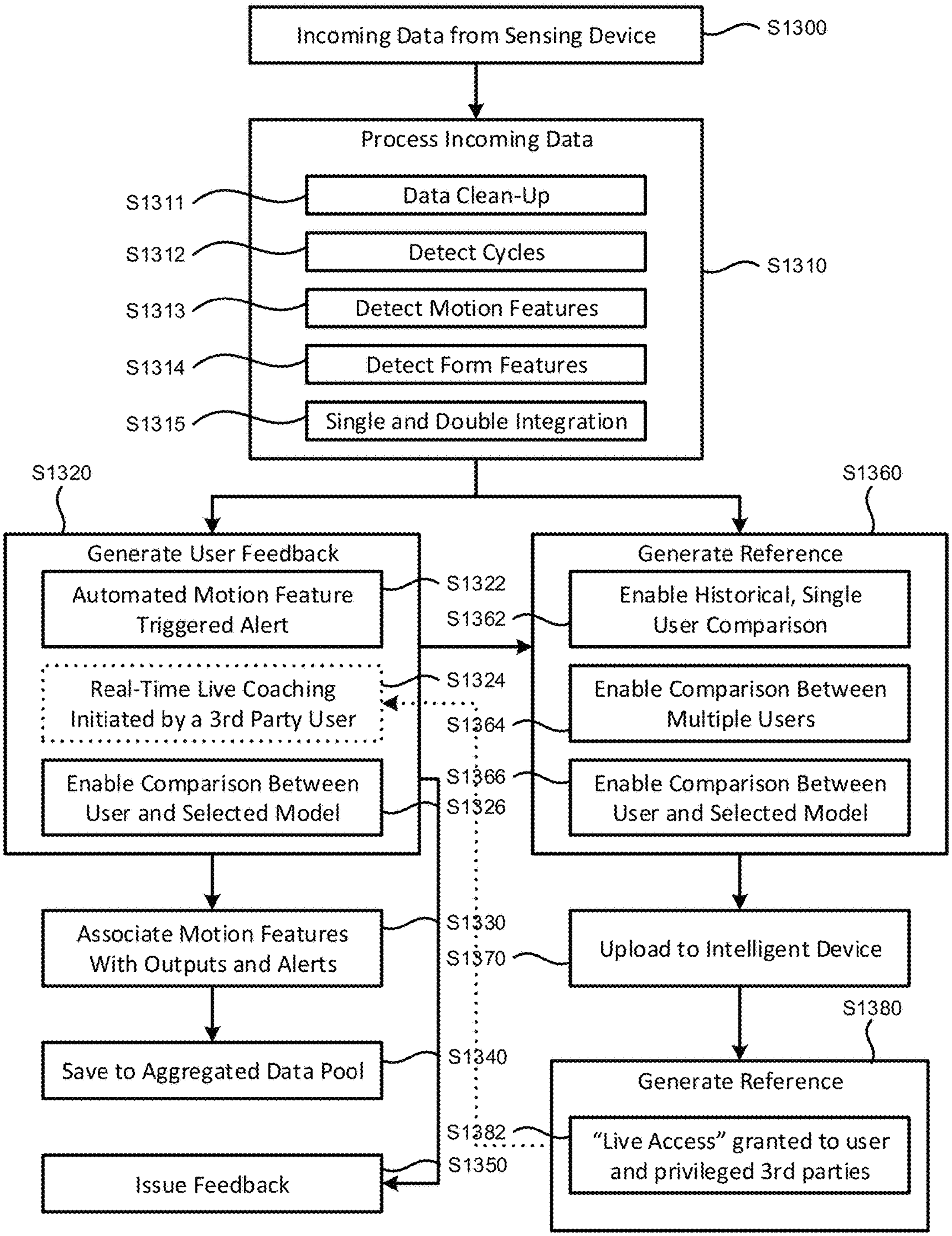
FIG. 5 illustrates a flowchart of a method of processing data from the intelligent device in accordance with an embodiment.

FIG. 5 illustrates operation of the server in accordance with an embodiment. First, the incoming data from the ID is received (S1300). Then, the incoming data is processed (S1310), e.g., cleaned up and transformed into the body frame (S1311), cycles detected (S1312), motion features detected (S1313), form features detected (S1314), and any single and double integration performed (S1315).

Cycle detection capabilities (S1312) allows isolation of a single cycle for future visualization. These cycles may be superimposed on one another or otherwise displayed such that the user can distinguish variations in the feature or cyclic path through time. In some implementations, this cycle may be compared to a model, ideal, or norm of these cycles to distinguish variation.

These motion features (MF) include, but are not limited to, pronation, hip-drop, stride length, foot strike, hip tilt, hip rotation, toe rotation, and others. In some implementations patterns, thresholds, or sequences of MF may be used to initiate cues, alerts, or other communications with the user. These cues as well as the feedback message can be set in multiple ways including but not limited to the following:

(1) patterns, thresholds, or sequences may be determined by the ID platform (IDP) system using a series of known norms for the MF in question and cues are automatically generated and issued by the IPD to the user;

(2) patterns, thresholds, or sequences may be selectively set manually by the user;

(3) cues or communications may be selectively set manually by the user;

(4) patterns, thresholds, or sequences may be set automatically using hybrid information from both users and known norms; and/or (5) the IDP may otherwise enable communications between users in real time.

In the stand alone mode, a reference may be generated (S1360). This may include enabling an historical, single user comparison (S1362), a comparison between multiple users (S1364), and/or a comparison between the user and a selected model (S1366). This reference may then be uploaded to the ID (S1370). Visualizations may be generated (S1380) and may include granting live access to the user and non-SD users referred to as privileged third parties (S1390).

The selected model may be a user's typical form, e.g., for a particular activity, such as a particular distance, may be an ideal form, may be a form of another particular individual, and so forth. User data and visualizations can be selectively compared to that of other users in such a way as to highlight form similarities and differences. This can be done to create tools for training, rehabilitation, etc. comparing general users to professional users, members of a team, competitors, and/or other scenarios. The selected model may also be used to directly compare a single user's form metrics or performance metrics in various points in time. One example could include the comparison of an athlete's profiles during a peek performance, directly prior to injury, and during recovery.

Streaming data and corresponding user or third party communications, cues, or inputs may be associated and aggregated to generate a system of data or motion feature traits and cues. These cues may be tagged, sorted, or otherwise organized and associated with data or motion features traits such that they may among other things be utilized as automated communications in implementation with a wider user base or to create new user norms.

Such information may be used by non-trained individuals/non technicians, outside the lab environment, and may be used as a complementary device to lab-based, high accuracy, high fidelity systems as an extension into non-controlled environments. Simple visual interface highlights important gait features without the need for technical interpretation of data outputs by user.

Figure 6:
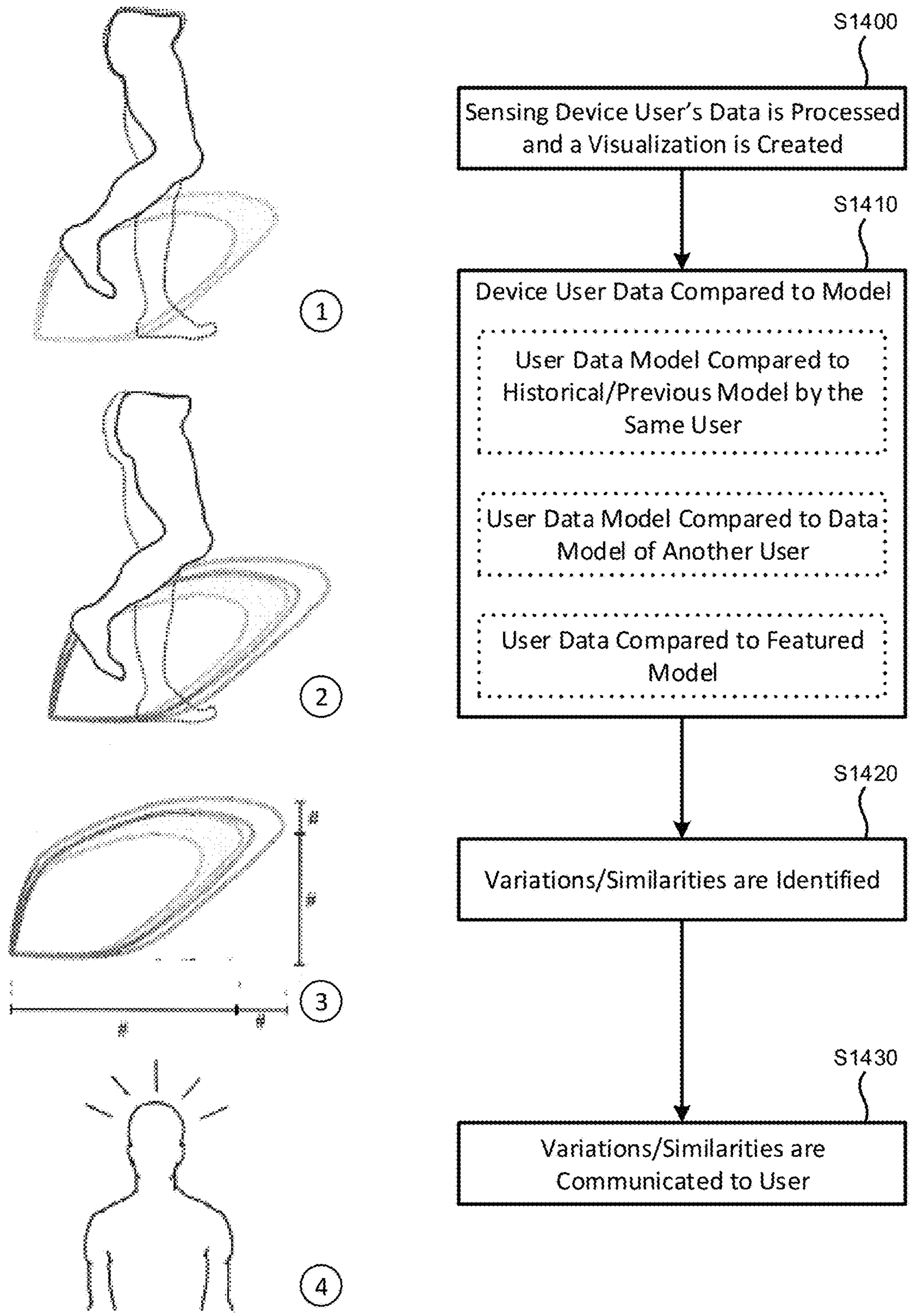
FIG. 6 illustrates a flowchart of a method of comparing the binodal sensing device data to a reference in accordance with an embodiment.

An example of a method of visualization is illustrated in FIG. 6. First, the ID or the server uses data from the SD to create a visualization of the movement of the user (S1400). Then, this data is compared to a selected model, discussed above (S1410). Then, similarities/differences are identified (S1420). These similarities/differences are then communicated to the user or other privileged party (S1430).

When the system is operating in live stream mode, or when live access is granted, in addition to all of the functions described with reference to the stand-alone mode, user feedback may be generated (S1320). Such user feedback may include automated motion feature triggered alert (S1322), real-time live coaching by a third party user (S1324), and/or feedback generated from comparing a user's current MF and a selected model (S1326).

Real-time coaching may use visuals and metrics constructed for the SD user accessible to any users on the same or associated account of the IDP. A non-user of the SD may therefore watch the SD user's IDP visualizations (described below with reference to FIG. 6) or metrics in real time and communicate with or coach the SD user during activity.

The user feedback may then be provided to the ID and/or the SD (S1350). The user feedback may also be used to associate motion features with outputs and alerts (S1330), which may then be saved to an aggregated data pool (S1340). User feedback can be tagged, sorted, or otherwise organized and associated with data or motion feature traits such that they may be utilized as automated communications in implementation with a wider user base.

The SD, the ID, and the server or cloud, are all in communication with each other. A single SD or multiple SD's can be used with the system. Since the data from the SD's can be viewed on multiple IDP's the system can be used with one to a plurality of SD's and ID's in any number of permutations. The SD may perform minimal processing and may primarily collect, compress, store, and upload data as indicated by the profile. The majority of the processing detailed above may be performed by the ID and/or in the Cloud, as appropriate. The SD may utilize a rechargeable battery, or any battery or power source, for operation.

By way of summation and review, current biomechanics analysis and motion capture technologies utilize a plurality of cameras and/or rigid units containing one inertial sensor deployed in a network to capture the position of a body segment in three-dimensional space. The SD described above differs distinctly from current devices by utilizing a plurality of inertial sensors, e.g., two sensors, within a single, non-rigid unit to, among other things, identify a segment's position in space, identify internal movement and stability such as torsion, bending, shear movement, etc. in the segment, and/or between two segments. The SD may function as a stand-alone data capture device or as a component of a greater motion and stability monitoring system.

The methods, processes, and/or operations described herein may be performed by code or instructions to be executed by a computer, processor, controller, or other signal processing device. The computer, processor, controller, or other signal processing device may be those described herein or one in addition to the elements described herein. Because the algorithms that form the basis of the methods (or operations of the computer, processor, controller, or other signal processing device) are described in detail, the code or instructions for implementing the operations of the method embodiments may transform the computer, processor, controller, or other signal processing device into a special-purpose processor for performing the methods described herein.

The embodiments described herein may be implemented in logic which, for example, may include hardware, software, or both. When implemented at least partially in hardware, the embodiments may be implemented, for example, any one of a variety of integrated circuits including but not limited to an application-specific integrated circuit, a field-programmable gate array, a combination of logic gates, a system-on-chip, a microprocessor, or another type of processing or control circuit.

When implemented in at least partially in software, the embodiments may include, for example, a memory or other storage device for storing code or instructions to be executed, for example, by a computer, processor, microprocessor, controller, or other signal processing device. The computer, processor, microprocessor, controller, or other signal processing device may be those described herein or one in addition to the elements described herein. Because the algorithms that form the basis of the methods (or operations of the computer, processor, microprocessor, controller, or other signal processing device) are described in detail, the code or instructions for implementing the operations of the method embodiments may transform the computer, processor, controller, or other signal processing device into a special-purpose processor for performing the methods described herein.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed:

1. A method of analyzing motion data derived from inertial sensors affixed to a body using an intelligent device, the method comprising:

receiving, via wireless transmission, raw three-dimensional motion data at the intelligent device, wherein the raw three-dimensional motion data is derived from one or more of the inertial sensors affixed to the body;

processing, via a processor, the raw three-dimensional data into translatable data points, the processing method comprising one or more of:

cleaning the data to eliminate noise;

detecting cycles in the data and isolating these cycles;

detecting motion features in the data comprising pronation, hip-drop, stride length, foot strike, hip tilt, hip rotation, and toe rotation;

detecting form features in the data; and performing single and double integrations on the data;

deriving specified metrics from the processed data comprising one or more of a stride length, an impact force, a pace, and a cadence; and communicating, in real-time, a portion of derived specified metrics to the user via a visual interface.

2. The method of claim 1, further comprising receiving three-dimensional data by at least one of: live-streaming the data and uploading the data at a later time.

3. The method of claim 1, further comprising sending data back to the intelligent device for further processing after being uploaded to the server.

4. The method of claim 1, further comprising initiating cues, alerts, or other communications with the user upon recognition of specified metrics or motion features, wherein the cues, alerts, or other communications are set by at least one of:

manually set by the user or automated by the intelligent device.

5. The method of claim 4, further comprising initiating communication with the user, wherein initiating communication with the user utilizes at least one of: patterns, thresholds, and sequences within the specified metrics or motion features as determined by the intelligent device or set by the user.

6. The method of claim 1, further comprising comparing multiple sets of data, wherein the comparing of multiple sets of data comprises at least one of: a single user comparing an historical data set to a current data set, a comparison between multiple users, and a comparison between a single user's data set to an ideal form.

7. The method of claim 1, further comprising highlighting the gait analysis results via a simple user interface.

8. The method of claim 1, further comprising using motion-triggered cues to dynamically change the settings on the device during use.

9. The method of claim 1, further comprising reducing noise in the signal by minimizing device inertia and by rendering the device immobile on the surface of the skin.

10. The method of claim 1, wherein the inertial sensors are affixed to the body via an adhesive.

11. The method of claim 1, further comprising:

outputting processed data back to the sensing device or the user;

uploading the processed data to a server;

directly comparing the derived specified metrics at one or more points in time;

identifying one or more similarities or differences of the derived specified metrics at the one or more points in time; and communicating the one or more similarities or differences to the user via the visual interface.

* * * * *